(12) United States Patent
Howarth et al.

(10) Patent No.: US 7,651,860 B2
(45) Date of Patent: Jan. 26, 2010

(54) METHOD OF ANALYZING LOW LEVELS OF PEROXYACETIC ACID IN WATER

(75) Inventors: Jonathan N. Howarth, Modesto, CA (US); Michael S. Harvey, Modesto, CA (US)

(73) Assignee: Enviro Tech Chemical Services, Inc., Modesto, CA (US)

( * ) Notice: Subject to any disclaimer, the term of this patent is extended or adjusted under 35 U.S.C. 154(b) by 613 days.

(21) Appl. No.: 11/015,577

(22) Filed: Dec. 17, 2004

(65) Prior Publication Data

US 2006/0134795 A1    Jun. 22, 2006

(51) Int. Cl.
*G01N 33/00* (2006.01)

(52) U.S. Cl. .................. 436/100; 422/68.1; 422/75; 422/100

(58) Field of Classification Search .............. 436/100; 422/68.1, 75, 100
See application file for complete search history.

(56) References Cited

OTHER PUBLICATIONS

Howarth, Jonathan. "Decay Kinetics of Peroxyacetic Acid (PAA) and Hydrogen Peroxide in a Variety of Water Matrices." Aug. 20, 2003, pp. 1-19.*
Wagner, M.; Brumelis, D.; and Gehr, R. Disinfection of Wastewater . . . Treated Municipal Effluent. Water Environment Research, 74: 33-50. (2002).
Bolognesi, C.; Buschini, A; Branchi, E.; et al. Comet and micronucleus . . . different disinfectants. Science of the Total Environment, 333: 127-136. (2004).
Franson, Mary Ann H. (editor). Standard Methods for . . . and Wastewater, "DPD Colorimetric Method." pp. 4-63-4-64, Published by APHA, AWWA, WEF, 20th edition. (1998).

* cited by examiner

*Primary Examiner*—Sam P Siefke
(74) *Attorney, Agent, or Firm*—Audrey A. Millemann; Weintraub Genshlea et al.

(57) ABSTRACT

Methods of analyzing low levels of peroxyacetic acid (PAA) in water are described. These methods employ buffering the PAA-containing water and the use of a N,N-diethyl-p-phenylenediamine (DPD) indicator system in the presence of iodide ion. The intensity of the pink coloration that develops is quantitated by colorimetric or titrimetric methods and correlated to the ppm PAA in the water. Positive interference effects due to the presence of hydrogen peroxide are eliminated by performing the analyses quickly after the introduction of the reagents.

13 Claims, No Drawings

METHOD OF ANALYZING LOW LEVELS OF PEROXYACETIC ACID IN WATER

BACKGROUND OF THE INVENTION

1. Field of the Invention

The invention relates to analytical methods for measuring low levels of peroxyacetic acid (also known as peracetic acid) in water.

2. Description of the Related Art

Peroxyacetic acid (PAA)-hydrogen peroxide (HP) equilibrium products are available from several manufacturers in the United States. The products are currently under consideration as chlorine alternatives in wastewater disinfection when applied in the range of about 1-10 ppm as PAA. In order for these products to be permitted in municipal wastewater applications, the results of aquatic toxicology tests, efficacy tests and field trials result must be presented to government regulatory agencies. Without a simple, accurate, reliable, and readily-available test procedure for PAA, the results of such tests would be meaningless. The various regulatory agencies require disinfectant-type products to be measured and monitored routinely during the treatment process so as to gauge the effectiveness of the treatment and estimate the impact of the chemical on the environment.

PAA-HP equilibrium products are also dosed to several other water systems in the 1-10 ppm range for control of bacteria, algae, fungi, and slime in recirculating cooling towers, reverse osmosis, and ultra filtration systems. Minimum levels of PAA must be maintained in order to ensure that the anticipated disinfection results are achieved. Here again, there is a need for a simple, accurate, and inexpensive test procedure. In addition, because the test results are used to determine the feed rates, an erroneous or unreliable test method may increase the cost to the end user by unnecessarily requiring the use of more PAA. Therefore, accurate and reliable testing methods are important to control costs, as well as to assure system integrity and to protect and monitor our environment.

There are several different types of reagent test kits available to determine PAA in water. Some are based on test strips consisting of a pad impregnated with an indicator reagent that changes color in response to the concentration of the PAA analyte. The user dips the test strip in the water for a few seconds and matches the color response to a comparator chart corresponding to the analyte concentration. Test strips suffer notorious deficiencies well known to those skilled in the art. The indicator reagent may leach from the pad when immersed in water to make color comparison impossible. Any color that does develop is strongly dependent on the length of time the strip is immersed, and the length of time after immersion until the color comparison is made. In addition, because the test strip method is a subjective test, its accuracy is limited. Consequently, although test strips are convenient to use, they are not accurate enough for reliable measurements.

Another test kit is based on the ceric IV sulfate-sodium thiosulfate titration reaction that employs a ferroin indicator. This technique can only be used when the concentration of the PAA is greater than 30 ppm, making it unsuitable for the low levels necessary in water, wastewater, and recirculating cooling water systems.

A commercially available test kit from CheMetrics based on dimethyl-substituted N,N-diethyl-p-phenylenediamine (DDPD) boasts a much lower detection limit of 0.5 ppm PAA. In this method, the user treats the sample with an excess of potassium iodide. A one-minute reaction time permits the PAA to oxidize the iodide to iodine. The sample is then introduced to a solution of DDPD indicator, which forms a purple color in direct proportion to the PAA concentration. Color comparator tubes or a pre-calibrated spectrophotometer set to 565 nm are used to quantitate the amount of PAA present. This method has a number of limitations. For example, although it provides reliable and reproducible results in deionized water, the opposite is true in natural waters, even clean drinking water. It is uncertain why this method exhibits these irregularities. It may be related to underbuffering of the DDPD solution which causes the pH to swing outside the 6.2-6.5 range for optimum development of the indicator. The results are therefore unreliable for any diluted solution of peroxyacetic acid, with the exception of deionized or distilled water.

Another method, developed by Wagner et al., *Water Environment Research*, vol. 74, p. 33 (2002), uses the 2,2'-azino-bis(3-ethylbenz-thiazoline-6-sulfuric acid) diammonium salt (ABTS)-horseradish peroxidase (HRP) assay with a spectrophotometer set to 405 nm. This method is accurate and reliable, but is quite cumbersome and difficult to perform, and requires reagents that are expensive and difficult to obtain. This procedure is not amenable for field use or manipulation due to its complexity, costs, time requirement to perform the analysis, and availability of reagents. In addition, any reading over 1 mg/l must be diluted and analyzed again to obtain solutions <1 mg/l.

A common method for analyzing low levels of chlorine in treated waters is the N,N-diethyl-p-phenylenediamine (DPD) indicator-colorimetric method approved by the United States EPA. To measure free chlorine, the DPD indicator is introduced to the water along with a buffer system to adjust the pH to 6.2-6.5. Free chlorine instantly oxidizes the DPD indicator to give a pink coloration, the intensity of which is proportional to the amount of free chlorine in the sample. To measure total chlorine, an iodide ion catalyst and a two-minute reaction time are required to quantitatively liberate iodine, the species that oxidizes the DPD indicator to the pink coloration. A spectrophotometer is then used that is programmed to measure the intensity of the pink coloration and display the results in terms of ppm free or total chlorine. Alternatively, the intensity of the coloration may be measured using a color comparator method that yields a result to corresponding to the chlorine concentration.

Despite the similar chemical properties of PAA and chlorine, however, the standard DPD indicator-colorimetric method has been found unsuitable for determining low levels of PAA. Unlike free chlorine, PAA does not instantly oxidize the DPD indicator when introduced to the water sample with a pH buffer. Moreover, when the PAA solution is exposed to the DPD indicator, pH buffer, and iodide ion combination, the hydrogen peroxide that always accompanies PAA oxidizes the DPD indicator to a significant extent during the two-minute reaction time. The result is a large false positive interference to the PAA response. Certainly, the hydrogen peroxide interference was recognized by Bolognesi et al., *Science of the Total Environment*, vol. 333, p. 127 (2004), who removed the hydrogen peroxide interference by pretreating the sample with a catalase enzyme and potassium iodide followed by use of a "total DPD reaction" for determining the PAA concentration.

Thus, there is a need for a method of analyzing a low level of PAA that is simple to use, accurate, and reliable. The method should use readily-available inexpensive reagents, and be amenable to packaging in the form of a portable kit for real-time measurements in the field. This invention addresses those needs.

SUMMARY OF THE INVENTION

The invention is a method of analyzing low levels of PAA in water. The method is highly accurate, reliable and very easy to perform. It permits the determination of PAA at levels useful in water sanitation.

The first embodiment of the invention is a method which uses an N,N-diethyl-p-phenylenediamine (DPD) indicator for measuring low levels of PAA in water. The present inventors have discovered that, in the presence of iodide ion, a buffered solution of PAA rapidly and quantitatively oxidizes iodide ion ($I^-$) into iodine ($I_2$) which then reacts with the DPD indicator to turn the solution a shade of pink, the intensity of which is proportional to the concentration of the PAA. A spectrophotometer may be used that is programmed to measure the intensity (absorbance) of the pink coloration and display the result in terms of ppm of chlorine [as $Cl_2$]. Alternatively, the intensity of the pink coloration may be determined using a color comparator technique. A simple calculation can then be performed to convert the test result (ppm of chlorine) into ppm of PAA, based on the molecular weight ratio of PAA to $Cl_2$ (76:71 or 1.07).

It has also been discovered that HP does not interfere with the measurement of PAA provided that the analysis is completed within 30 seconds of combining a buffered solution of PAA, the DPD indicator, and iodide ion.

The second embodiment of the invention is a method that is the same as the first embodiment, except that the pink coloration is elucidated by titration to a clear end point with a standard solution of ferrous ethylenediammonium sulfate.

DETAILED DESCRIPTION OF THE INVENTION

The present invention is a method for measuring the level of PAA in water treated with PAA-HP equilibrium products. The method uses either colorimetry (a spectrophotometer or color comparator technique) or titration, and preferably includes the steps set forth below.

Method Using Spectrophotometer Colorimetry

A sample of the water to be tested is obtained. Water samples of 5, 10, or 25 mls are convenient to use. The steps described below pertain to a 10 ml sample. The sample must be analyzed immediately, as it cannot be preserved for subsequent analysis.

A spectrophotometer capable of measuring chlorine using the DPD colorimetric method is used. The Hach model 46700-00 is a suitable instrument for use with a 10 ml sample. Before testing, the spectrophotometer is set in the low (LO) range mode by checking that the display reads to the hundredths (0.00).

Two sample cells are filled to the 10 ml mark with the water sample. One cell is designated as the blank and the other as the prepared sample. The blank cell is capped and placed in the cell compartment in the spectrophotometer. The instrument is zeroed and the blank cell is removed.

Next, DPD indicator, buffer, and iodide ion are added to the prepared sample cell. These three reagents may combined together before adding to the prepared sample cell, or the buffer may be added to the prepared sample cell first, followed by a mixture of the DPD indicator and iodide ion. A suitable buffer is a phosphate buffer system, although other buffer systems may be used. Enough buffer is added to the sample cell to adjust the pH to between about 6.2 and about 6.5. Sufficient DPD indicator and iodide ion are added to bring the pink coloration into the working range of the spectrophotometer used. For example, if the Hach model 46700-00 spectrophotometer is used, the working range is about 0 to about 2.2 ppm PAA. For a 10 ml sample, at least about 19.2 µg of iodide ion and at least about 25 µg of DPD indicator are used. A preferred source of iodide ion is potassium iodide, although other iodide salts, such as sodium iodide, lithium iodide, or cesium iodide may be used. If potassium iodide is used with the Hach model 46700-00 and a 10 ml sample, then about at least 25 µg of potassium iodide is preferably used. A preferred source of DPD indicator is the DPD oxalate salt.

Alternatively, the DPD indicator, buffer, and iodide ion may be added to the prepared sample cell in the form of a DPD total chlorine reagent powder pillow (such as those made by Hach, Taylor Technologies, LaMott, and CheMetrics). For a 10 ml sample, Hach product #21056-69 is appropriate. Care must be taken not to use a DPD free chlorine reagent powder pillow instead, as these do not work in this method.

In the presence of iodide ion, a buffered solution of PAA rapidly and quantitatively oxidizes the iodide ion ($I^-$) into iodine ($I_2$) which then reacts with the DPD indicator to turn the solution a shade of pink, the intensity of which is proportional to the concentration of the PAA.

The prepared sample cell is capped and shaken gently to mix the reagents. A pink color will develop, indicating the presence of PAA.

Within 30 seconds of adding the DPD indicator, the prepared sample cell is read. The resulting number is the apparent ppm total chlorine. The apparent ppm total chlorine is then converted to the actual concentration of PAA by multiplying the apparent ppm total chlorine by the molecular weight ratio of PAA to $Cl_2$ (76:71 or 1.07):

$$1.07 \times (\text{apparent ppm total chorine}) = \text{actual ppm PAA}$$

EXAMPLE 1

A series of tests were performed using a synthetic water matrix prepared to possess the water quality parameters shown in Table I.

TABLE I

| pH | Conductivity µS/cm$^{-1}$ | Total Alkalinity/ ppm as $CaCO_3$ | Total Hardness/ ppm as $CaCO_3$ |
|---|---|---|---|
| 7.3 | 341 | 60 | 74 |

The standard 0.1N ceric IV sulfate—0.1N sodium thiosulfate/iodometric analytical technique was used to determine that a freshly prepared equilibrium mixture contained 15.55% PAA, and 22.3% HP. This was used to prepare a stock solution containing 100 ppm PAA and 143.4 ppm HP by weighing 0.323 g into a 500 ml volumetric flask and making up to volume with deionized water. The freshly prepared solution was used to dose the synthetic water matrix. The first solution prepared was dosed to contain a nominal concentration of 2.0 ppm PAA. This was immediately analyzed for PAA using the DPD method described above. A total of five replicates was made. Thereafter, further dilutions were prepared and the process was repeated for each dilution.

Table II shows the mean concentration of PAA, residual standard deviation, and % recovery for the diluted solutions prepared in the synthetic water matrix.

TABLE II

| Nominal Concentration/ppm PAA | Mean Recovered Concentration/ppm PAA | Relative Standard Deviation | % Recovery |
|---|---|---|---|
| 2.00 | 1.988 | 0.027749 | 99.4 |
| 1.00 | 1.006 | 0.015166 | 100.6 |
| 0.50 | 0.516 | 0.018166 | 103.2 |
| 0.25 | 0.246 | 0.008944 | 98.4 |
| 0.1 | 0.095 | 0.009815 | 95.0 |
| 0.05 | 0.051 | 0.015945 | 102.0 |

Regression analysis software was used to calculate a correlation coefficient ($R^2$) of 0.9995, and the following mathematical relationship:

measured ppm PAA($Y$)=0.9954×nominal ppm PAA ($X$)+0.0034

A correlation coefficient of 0.9995 indicated that the hydrogen peroxide also present in solution did not interfere with the measurement of PAA. This is attributed to the fact that the analysis takes place rapidly in the calorimeter within 30 seconds of contact with the DPD/KI/buffer reagent combination.

The regression analysis data indicates that the method of the invention provides a highly selective and extremely accurate analysis of PAA. Over the concentration range of 0.05-2.00 ppm, analytical recoveries were close to quantitative in all cases.

Method Using Color Comparator Colorimetry

A sample of the water to be tested is obtained. Water samples of 5, 10, or 25 mls are convenient to use. The steps described below pertain to a 5 ml sample. The sample must be analyzed immediately, as it cannot be preserved for subsequent analysis.

A color comparator test kit capable of measuring chlorine using the DPD colorimetric method is used. The Hach model CN-66T is a suitable kit for use with a 5 ml sample.

Two viewing tubes are filled to the 5 ml mark with the water sample. One viewing tube is designated as the blank and the other as the prepared sample.

Next, DPD indicator, buffer, and iodide ion are added to the prepared sample tube. These three reagents may combined together before adding to the prepared sample tube, or the buffer may be added to the prepared sample tube first, followed by a mixture of the DPD indicator and iodide ion. A suitable buffer is a phosphate buffer system, although other buffer systems may be used. Enough buffer is added to the sample tube to adjust the pH to between about 6.2 and about 6.5. Sufficient DPD indicator and iodide ion are added to bring the pink coloration into the working range of the color comparator used. For example, if the Hach model CN-66T is used, the working range is about 0 to about 3.5 ppm PAA. For a 5 ml sample, at least about 9.6 µg of iodide ion and at least about 12.5 µg of DPD indicator are used. A preferred source of iodide ion is potassium iodide, although other iodide salts, such as sodium iodide, lithium iodide, or cesium iodide may be used. If potassium iodide is used with the Hach model CN-66T and a 5 ml sample, then about at least 12.5 µg of potassium iodide is preferably used. A preferred source of DPD indicator is the DPD oxalate salt.

Alternatively, the DPD indicator, buffer, and iodide ion may be added to the prepared sample tube in the form of a DPD total chlorine reagent powder pillow. For a 5 ml sample, Hach product # 14076-99 is appropriate. Care must be taken not to use a DPD free chlorine reagent powder pillow instead, as these do not work in this method.

The prepared sample tube is capped and shaken gently to mix the reagents. A pink color will develop, indicating the presence of PAA.

Within 30 seconds of adding the DPD indicator, the prepared sample tube and the blank sample tube are respectively placed in the top right and top left hand side openings of the color comparator, and the color disc is rotated until the colors in the two viewing windows match. The number in the scale window is then read as the apparent ppm total chlorine. The apparent ppm total chlorine is then converted to the actual concentration of PAA by multiplying the apparent ppm total chlorine by the molecular weight ratio of PPA to $Cl_2$ (76:71 or 1.07):

1.07×(apparent ppm total chorine)=actual ppm PAA

Method Using Titration

A sample of the water to be tested is obtained. The steps described below pertain to a 25 ml sample. The sample must be analyzed immediately, as it cannot be preserved for subsequent analysis.

Twenty five ml of the water sample is pipetted into an Erlenmeyer flask.

Then, DPD indicator, buffer, and iodide ion are added to the flask. These three reagents may be combined together before adding to the flask, or the buffer may be added first, followed by a mixture of the DPD indicator and iodide ion. A suitable buffer is a phosphate buffer system, although other buffer systems may be used. Enough buffer is added to the flask to adjust the pH to between about 6.2 and about 6.5. Sufficient DPD indicator and iodide ion are added to bring the pink coloration into the working range of the technique (about 0 to about 5 ppm PAA). For example, using a 25 ml sample, then at least about 48 µg of iodide ion and at least about 62.5 µg of DPD indicator are used. A preferred source of iodide ion is potassium iodide, although other iodide salts, such as sodium iodide, lithium iodide, or cesium iodide may be used. If potassium iodide is used, then about at least 62.5 µg of potassium iodide is preferably used. A preferred source of DPD indicator is the DPD oxalate salt.

Alternatively, the DPD indicator, buffer, and iodide ion may be added to the flask in the form of a DPD total chlorine reagent powder pillow (such as those made by Hach, Taylor Technologies, LaMott, and CheMetrics). For a 25 ml sample, Hach product #14064-99 is appropriate. Care must be taken not to use a DPD free chlorine reagent powder pillow instead, as these do not work in this method.

The flask is shaken gently to mix the reagents. A pink color will develop, indicating the presence of PAA.

Within 30 seconds of adding the DPD indicator, the solution is titrated with 0.00564 N ferrous ethylenediammonium sulfate solution to a colorless end-point. The number of ml of titrant required to affect this corresponds to the apparent ppm total chlorine. The apparent ppm total chlorine is then converted to the actual concentration of PAA by multiplying the apparent ppm total chlorine by the molecular weight ratio of PAA to $Cl_2$ (76:71 or 1.07):

1.07×(apparent ppm total chorine)=actual ppm PAA

We claim:

1. A method for determining the concentration of peroxyacetic acid in water, comprising:
   a) obtaining a sample of water to be tested;
   b) adding buffer, DPD indicator, and iodide ion to said sample;
   c) allowing a pink color to develop in said sample;

d) within 30 seconds of adding said DPD indicator, reading the apparent concentration of total chlorine in said sample using a colorimetry method; and e) converting said apparent concentration of total chlorine in said sample to the actual concentration of peroxyacetic acid in said sample.

2. The method of claim 1, wherein the amount of said buffer is sufficient to adjust the pH of said sample to between about 6.2 and about 6.5.

3. The method of claim 2, wherein the amount of said DPD indicator and said iodide ion are sufficient to bring said pink color of said sample into the working range of said colorimetry method.

4. The method of claim 2, wherein said iodide ion is potassium iodide.

5. The method of claim 1, wherein said buffer, said DPD indicator, and said iodide ion are added in the form of a DPD total chlorine reagent powder pillow.

6. The method of claim 1, wherein said colorimetry method is a spectrophotometer.

7. The method of claim 1, wherein said colorimetry method is a color comparator technique.

8. A method for determining the concentration of peroxyacetic acid in water, comprising:

a) obtaining a sample of water to be tested;

b) adding buffer, DPD indicator, and iodide ion to said sample;

c) allowing a pink color to develop in said sample;

d) within 30 seconds of adding said DPD indicator, reading the apparent concentration of total chlorine in said sample using a titration method; and e) converting said apparent concentration of total chlorine in said sample to the actual concentration of peroxyacetic acid in said sample.

9. The method of claim 8, wherein the amount of said buffer is sufficient to adjust the pH of said sample to between about 6.2 and about 6.5.

10. The method of claim 9, wherein the amount of said DPD indicator and said iodide ion are sufficient to bring said pink color of said sample into the working range of said titration method.

11. The method of claim 9, wherein said iodide ion is potassium iodide.

12. The method of claim 8, wherein said buffer, said DPD indicator, and said iodide ion are added in the form of a DPD total chlorine reagent powder pillow.

13. The method of claim 8, wherein said titration method uses ferrous diethylene-ammonium sulfate.

* * * * *